(12) United States Patent
Möhring et al.

(10) Patent No.: US 9,498,417 B2
(45) Date of Patent: Nov. 22, 2016

(54) BLEACHING AND COLOURING COMPOSITION FOR HAIR

(71) Applicant: KAO GERMANY GMBH, Darmstadt (DE)

(72) Inventors: Hartmut Möhring, Seeheim-Jugenheim (DE); Dominic Pratt, Groβ-Gerau (DE)

(73) Assignee: KAO GERMANY GMBH, Darmstadt (DE)

( * ) Notice: Subject to any disclaimer, the term of this patent is extended or adjusted under 35 U.S.C. 154(b) by 26 days.

(21) Appl. No.: 14/367,516

(22) PCT Filed: Dec. 20, 2012

(86) PCT No.: PCT/EP2012/076467
§ 371 (c)(1),
(2) Date: Jun. 20, 2014

(87) PCT Pub. No.: WO2013/092904
PCT Pub. Date: Jun. 27, 2013

(65) Prior Publication Data
US 2015/0328100 A1    Nov. 19, 2015

(30) Foreign Application Priority Data

Dec. 23, 2011  (EP) .................................. 11195634

(51) Int. Cl.
| | |
|---|---|
| *A61Q 5/10* | (2006.01) |
| *A61K 8/34* | (2006.01) |
| *A61K 8/49* | (2006.01) |
| *A61K 8/25* | (2006.01) |
| *A61Q 5/08* | (2006.01) |
| *A61K 8/02* | (2006.01) |
| *A61K 8/22* | (2006.01) |
| *A61K 8/23* | (2006.01) |

(52) U.S. Cl.
CPC .................. *A61K 8/34* (2013.01); *A61K 8/022* (2013.01); *A61K 8/22* (2013.01); *A61K 8/23* (2013.01); *A61K 8/25* (2013.01); *A61K 8/342* (2013.01); *A61K 8/347* (2013.01); *A61K 8/494* (2013.01); *A61K 8/4926* (2013.01); *A61K 8/4946* (2013.01); *A61Q 5/08* (2013.01); *A61Q 5/10* (2013.01); *A61K 2800/4324* (2013.01); *A61K 2800/592* (2013.01); *A61K 2800/882* (2013.01)

(58) Field of Classification Search
CPC ............ A61Q 5/10; A61Q 5/08; A61K 8/34; A61K 8/23; A61K 8/494; A61K 8/22
USPC ............................................................ 8/405
See application file for complete search history.

(56) References Cited

U.S. PATENT DOCUMENTS

| | | | | |
|---|---|---|---|---|
| 2006/0185098 | A1* | 8/2006 | Kravtchenko | A61K 8/22 8/405 |
| 2007/0067925 | A1* | 3/2007 | Javet | A61K 8/23 8/405 |
| 2011/0052518 | A1* | 3/2011 | Pratt | A61K 8/19 424/62 |

FOREIGN PATENT DOCUMENTS

| | | |
|---|---|---|
| EP | 1 598 052 A1 | 11/2005 |
| EP | 1 759 684 A1 | 3/2007 |
| EP | 1 759 685 A1 | 3/2007 |
| EP | 2 272 489 A1 | 1/2011 |
| JP | 2010024158 A * | 2/2010 ............... A61Q 5/10 |

OTHER PUBLICATIONS

STIC Search Report dated May 10, 2016.*
International Search Report dated Nov. 19, 2013, mailed Nov. 28, 2013.

* cited by examiner

*Primary Examiner* — Eisa Elhilo
(74) *Attorney, Agent, or Firm* — Norris McLaughlin & Marcus PA

(57) ABSTRACT

Present invention relates to an aqueous composition for bleaching and coloring hair which comprises direct dyes and an oxidizable solvent in addition to a compound with a bleaching effect, an alkalizing agent and an oxidizing agent. It is furthermore the object of the present invention is the use of oxidizable solvent, preferably an aromatic or aliphatic alcohol for stabilizing a direct dye in an aqueous composition comprising at least one compound with hair bleaching effect, at least one oxidizing agent and at least one alkalizing agent.

20 Claims, No Drawings

BLEACHING AND COLOURING COMPOSITION FOR HAIR

This application is a 371 application of PCT/EP2012/076467 filed Dec. 20, 2012, which claims foreign priority benefit under 35 U.S.C. §119 of European Application No. 11195634.8 filed Dec. 23, 2011, the disclosures of which are all incorporated herein by reference.

Present invention relates to an aqueous composition for bleaching and coloring hair which comprises direct dyes and an oxidizable solvent in addition to a compound with a bleaching effect, an alkalizing agent and an oxidizing agent.

Bleaching and dyeing hair are always done in two subsequent process as the most of the direct dyes if not all are not stable under highly oxidative conditions. In order to achieve darker and vivid colours this is essential. Exposure of hair to two different process one after another furthermore causes considerable hair damage.

The purpose of the present invention is to find out a new process wherein hair is bleached and coloured in the same process. In other words, the purpose is at the same time finding out a new composition wherein the direct dyes have considerably improved stability so that it allows achieving darker and vivid colours on hair.

The inventors of the present invention has found out that that a composition comprising a direct dye, at least one compound with bleaching effect, at least one oxidizing agent, at least one alkalizing agent and at least one oxidizable solvent bleaches and colours hair intensively due to the improved stability of the direct dye otherwise instable in the same system. At the same time the composition colours hair homogeneously especially hair with various parts with various degree of damage in its length. It is also observed that the composition is milder than the same composition without oxidizable solvent.

Thus, the first object of the present invention is an aqueous composition for bleaching and colouring hair comprising at least one direct dye, at least one compound with hair bleaching effect, at least one oxidizing agent, at least one alkalizing agent and at least one oxidizable solvent.

The second object of the present invention is the use of the composition for bleaching and colouring hair.

It is known in the art that bleaching compositions are prepared by mixing at least two compositions prior to application onto hair. Therefore, present invention is at the same time on a three part bleaching colouring composition for hair wherein the first part, Part A, is an anhydrous composition and comprises at least one direct dye, at least one compound with hair bleaching effect and at least one alkalizing agent, the second part, Part B, is an aqueous composition and comprises at least one oxidizing agent and the third part, Part C, comprises at least one oxidizable solvent.

Further object of the present invention is a method for bleaching and colouring hair wherein an aqueous composition is prepared by mixing immediately before use an anhydrous composition (Part A) comprising at least one direct dye, at least one compound with hair bleaching effect and at least one alkalizing agent, and an aqueous composition (Part B) comprising at least one oxidizing agent and a composition (Part C) comprising at least one oxidizable solvent and applied onto hair and after processing 5 to 45 min rinsed off from hair.

Further object of the present invention is a kit for bleaching and colouring hair comprising three of more compositions wherein it comprises a Part A which is an anhydrous composition and comprises at least one direct dye, at least one compound with bleaching effect and at least one alkalizing agent, and a Part B which is an aqueous composition comprising at least one oxidizing agent and a Part C comprising at least one oxidizable solvent.

With the term oxidizable solvent it is meant that the compound is oxidized under the conditions used to colour and bleach hair.

It is furthermore the object of the present invention is the use of oxidizable solvent, preferably an aromatic or aliphatic alcohol for stabilizing a direct dye in an aqueous composition comprising at least one compound with hair bleaching effect, at least one oxidizing agent and at least one alkalizing agent.

With the term anhydrous, it is meant that no additional water or any aqueous composition is added to the composition. However, it should be understood that the raw materials used may comprise water at low concentrations and therefore, from the experience, up to 1% water content does not have any influence on the stability and incorporated into compositions of the present invention in the form of bound water of individual chemicals.

Composition of the present invention comprises at least one direct dye. The direct dyes suitable are the ones generally known in the art such as anionic, cationic and nonionic ones. Plant dyes are also suitable for the compositions of the present invention.

Suitable anionic direct dyes in aqueous composition are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the most preferred anionic dyestuffs are Acid Red 52, DC Violet 2, DC Red 33, DC Orange 4, DC Red 27 and DC Yellow 10.

Suitable cationic dyes in aqueous composition are in principal those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87 and Basic Orange 31. The most preferred ones are Basic red 51, Basic Yellow 87 and Basic Orange 31 sold by CIBA.

Additionally, the aqueous compositions of the present invention may comprise neutral dyes (HC dyes), so called nitro dyes for shading purposes. Some examples to those are: HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

Further suitable direct dyes which are anionic under alkaline conditions are according to the following structures:

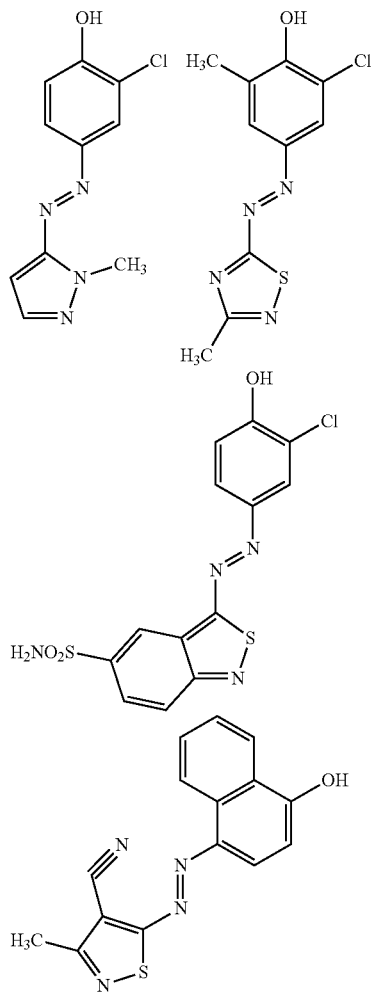

From the above disclosed direct dyes the preferred are anionic and nitro dyes and most preferred are anionic direct dyes.

According to the invention, the composition comprises one or more direct dye at a concentration of 0.01 to 10%, preferably 0.05 to 7.5% and more preferably 0.2 to 5% by weight calculated to the total composition. The composition can also comprise mixture of several direct dyes i.e. an anionic, a cationic and/or a nonionic ones. In such a case the dyes may be mixed at any ratio with each other.

The above mentioned direct dyes of cationic, anionic and nonionic character are preferably comprised in the water free bleaching composition at the concentration given in the above paragraph. The direct dyes of different characters can certainly be mixed as well.

Compositions of the present invention comprise at least one compound with hair bleaching effect. Suitable compounds are in general peroxides. Useful as such are in particular persulfates such as sodium and potassium persulfate, ammonium persulfate, earth alkali peroxides such as magnesium peroxide, melamine peroxide or urea peroxide or phtholimidoperoxy hexanoic acid. The proportion of peroxides is at least 5%, preferably in the range of 10 to 80%, more preferably 15 to 60% and most preferably 20 to 50% by weight, calculated to total composition. The compounds with hair bleaching effect are comprised preferably in anhydrous composition (Part A)

According to the invention, the anhydrous composition can also comprise 0.1% to 10% by weight, calculated to total composition prior to mixing with oxidizing lotion, at least one ammonium salts. Suitable ammonium salts are ammonium carbonate, ammonium hydrogen carbonate, ammonium carbamate, ammonium chloride, ammonium sulfate, ammonium phosphates, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate, ammonium acetate, ammonium formiate and ammonium lactate. Compositions may also comprise mixture or ammonium salts.

Preferred thereof are the ammonium phosphates, such as $NH_4H_2PO_4$, $(NH_4)_2HPO_4$, $(NH_4)_2NaPO_4$, $NaNH_4HPO_4$ or $NH_4Na_2PO_4$, ammonium chloride, ammonium sulfate and diammonium hydrogen citrate, as well as ammonium chloride.

As known from EP 609 796 A2, the ammonium compounds can also be used as sole bleaching agent in respectively higher amounts.

The total proportion of the compounds with bleaching and/or highlighting effect preferably ranges from 5% to 85%, preferably 10% to 80%, more preferably 15 to 70% and most preferably 20 to 60% by weight calculated to total composition.

Anhydrous composition comprises at least one alkalizing agent. Preferred alkalizing agent is sodium metasilicate and preferably comprised at a concentration 1 to 20% by weight calculated to the total composition. It should be noted that the composition applied onto hair is an alkaline composition and main alkalizing agent is in the anhydrous composition and the concentration must be enough to achieve a pH between 8 and 12. The pH of the ready to use product, mixture of bleaching composition, oxidizing lotion and oxidizable solvent, is preferably in the range of 8 to 11.5, in particular between 9 and 11.

In addition to the active component, anhydrous compositions also comprise the components customarily used in such compositions: In particular inert pulverulent carrier materials, these are for example, pyrogenic silicium dioxide, starch powder, etc., surface-active substances, binding agents, etc. In order to avoid repetition, reference is made to the respective standard literature, for example, K. Schrader and A. Domsch, "Cosmetology—Theory and Practice (2005, Verlag für Chemische Industrie), pages 142 to 151.

The ready to use composition is prepared by mixing the components with a composition comprising at least one oxidizing agent (Part B). The oxidizing agents suitable are hydrogen peroxide, urea peroxide, melamin peroxide or perborate salts. The most preferred is hydrogen peroxide. Such composition comprises 2 to 12% by weight at least one oxidizing agent preferably hydrogen peroxide and is either a solution or in the form of an emulsion.

The compositions of the present invention comprises at least one oxidizable solvent. With the term oxidizable it is meant that the solvent is oxidized, at least partly, which may also be as a whole under the conditions used for bleaching and colouring hair.

Suitable solvents are aromatic or aliphatic alcohols and preferably comprise only one OH group in its molecule. Preferably the aromatic alcohols have a Log P value (octanol water partition coefficient) at 25° C. in the range of 0 to 2.5, preferably in the range of 0.05 to 2, more preferably 1 to 2 and most preferably 1.1 to 1.7. Suitable aromatic oxidizable alcohols are 2-phenoxyethanol, benzyl alcohol, 2-phenylethanol and 2-benzyloxyethanol. Suitable aliphatic alcohols are isopropanol, propanol, n-butanol, isobutanol, t-butanol and 1-pentanol.

Most preferred oxidizable organic alcohols are the aromatic alcohols and among the aromatic oxidizable solvents benzyl alcohol, 2-phenoxyethanol, 2-phenylethanol are most preferred ones. Particularly preferred is/are benzyl alcohol and/or 2-phenoxyethanol and/or 2-phenylethanol.

At least one oxidizable solvent is comprise in the composition of the present invention is at a concentration below 8%, preferably 0.5 to 7.5% and more preferably 1 to 6% and most preferably 1 to 5% by weight calculate to the total composition.

Compositions of the present invention may comprise one or more of the ingredients disclosed in the following. They may be comprised in one or more parts of Part A, B and C. In the selection of particular composition compatibility of the selected ingredient in the particular part of the composition must be taken into account in case the compositions are prepared by mixing the parts after a long storage period.

Composition of the present invention may further comprise lipophilic ingredients such as vegetable oils, for example, jojoba oil or any other; petrolatum liquid paraffins, especially paraffinum perliquidum and paraffinum subliquidum; silicone oils; hydropobic fatty acid esters such as octyl palmitate, isocetyl palmitate, isopropyl palmitate and octyl stearate, $C_{10}$- to $C_{36}$-fatty acid triglycerides, as well as their mixtures. In the case that the use is wished among those the most preferred ones are silicone oils, jojoba oil, fatty acid esters, paraffin oils, combinations of fatty acid esters and paraffin oils. Fatty acid esters and/or paraffin oils and/or silicone oils are particularly preferred. Concentration of these lipophilic compounds are used in a total amount of about 0.1 to 20 percent by weight, preferably from 1 to 15 percent by weight, and more preferably from 2 to 10 percent by weight, calculated to total composition prior to mixing with oxidizing lotion.

In principal any silicone oil is useful as a lipophilic compound. Preferred are arylated silicones as a lipophilic ingredient at a concentration range of 0.1 to 50%, preferably 0.5 to 40% more preferably 1 to 35% and most preferably 2.5 to 30% by weight calculated to total composition prior to mixing with oxidizing lotion. Non-limiting suitable examples are phenyl methicone, phenyl trimethicone, diphenyl dimethicone, diphenylsiloxy phenyl trimethicone, tetraphenyl tetraphenyl trisiloxane, triphenyl trimethicone, tetramethly tetraphenyl trisiloxane and pentaphenyl trimethyl trisiloxane.

In the preferred embodiment of the present invention, the arylated silicone comprises at least 2 phenyl groups, more preferably 3 and most preferably 5 phenyl groups in its molecule.

Particularly preferred arylated silicone is pentaphenyl trimethyl trisiloxane available from Dow Corning under the trade name DC PH-1555 HRI.

It should be noted that compositions of the present invention can also comprise more than one arylated silicone.

Further, compositions may comprise polymers selected from the group consisting of cellulose polymer compounds, alginate, polysaccharides and acrylic acid polymers, preferably methyl cellulose compounds, ethyl cellulose compounds, hydroxyethylcellulose compounds, methylhydroxyethylcellulose compounds, methylhydroxypropylcellulose compounds, carboxymethyl cellulose compounds, alginic acids, sodium alginates, ammonium alginates, calcium alginates, gum arabic, guar gum or xanthan gum, or acrylic acid polymers with molecular weights from about 1,250,000 to 4,000,000, alone or in combination with each other. The polymers are used in a total concentration of 0.1 to 15%, preferably from 0.2 to 10%, and more preferably in an amount of from 0.5 to 7.5% by weight, calculated to total composition.

Composition can also comprise cationic polymers as conditioning and/or thickening agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 4, Polyquaternium 6, Polyquaternium 7, Polyquaternium 10, Polyquaternium 11, Polyquaternium 16, Polyquaternium 22, Polyquaternium 24, Polyquaternium 28, Polyquaternium 30, Polyquaternium 37, Polyquaternium 36, Polyquaternium 46, Polyquaternium 67, and Polyquaternium 72.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

Typical concentration range for any of the cationic conditioners mentioned above can be 0.1-7.5% by weight, preferably 0.3-5% by weight and more preferably 0.5-2.5% by weight, calculated to total composition Especially the composition comprising at least one oxidizing agent (Part B) may be in the form of emulsion, solution, dispersion and/or gel. Emulsion is the preferred form.

In the case the composition is in the form of an emulsion, it comprises as an emulsion base at least one fatty alcohol or mixture of fatty alcohols with the chain length of 14 to 22 C atoms. Examples to suitable fatty alcohols, without limiting the choice, are myristyl alcohol, cetyl alcohol, stearyl alcohol, behenyl alcohol and cetostearyl alcohol. The most preferred is cetostearyl alcohol well known with its trade name Lanette O or as Lanette N in mixture with sodium cetearyl sulfate from Cognis.

The concentration of fatty alcohol(s) is in the range from 0.5 to 20%, preferably 1 to 15% by weight, calculated to total composition prior to mixing with oxidizing and bleaching and/or highlighting composition.

Compositions according to present invention may comprise surfactants selected from anionic, nonionic, amphoteric (or zwiterionic) and/or cationic surfactants as emulsifier or solubilizer. Cationic surfactants are as well used as hair conditioners in the compositions.

Anionic surfactants suitable within the scope of the invention are in principal known from the cleansing compositions These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof as well as alkyl amido polyether carboxylic acids and salts thereof. Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants.

An overview of the anionic surfactants suitable for the present invention can furthermore be found in the monography of K. Schrader, "Grundlagen and Rezepturen der Kosmetika", $2^{nd}$ Ed. (1989, Hüthig Buchverlag), pp. 595-600 and pp. 683 to 691.

Further surfactants in the compositions according to the invention are nonionic surfactants alone or in admixture with anionic surfactants. These are described as well in Schrader, I.c., on pages 600-601 and pp. 694-695. Especially suited nonionic surfactants are, for example, long-chain fatty acid mono- and dialkanolamides, such as coco fatty acid mono- or diethanolamide and myristic fatty acid mono or diethanolamide, stearic acid mono or diethanolamide. Further nonionic surfactants suited are alkyl polyglucosides with an alkyl group of 8 to 18 carbon atoms, and with 1 to 5 glucoside units. Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates. Further nonionic surfactants preferred in the dyeing compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 25, preferably about 10 and about 20.

As further surfactant component, the compositions according to the invention can also contain amphoteric or zwitterionic surfactants. Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Composition can contain cationic surfactants as emulsifier, solubilizer and/or conditioning ingredients according to the formula, but not limited to.

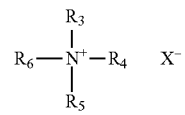

where $R_3$ is a saturated or unsaturated, branched or linear alkyl chain with 8-22 C atoms or

where $R_7$ is saturated or unsaturated, branched or linear alkyl chain with 7-21 C atoms and n has typical value of 1-4 or

where $R_8$ is saturated or unsaturated, branched or linear alkyl chain with 7-21 C atoms and n has typical value of 1-4, and $R_4$ is H or unsaturated or saturated, branched or linear alkyl chain with 1-22 C atoms or

or

where $R_7$, $R_8$ and n are same as above.

$R_5$ and $R_6$ are H or lower alkyl chain with 1 to 4 Carbon atoms, and X is typically chloride, bromide, methosulfate.

Typical examples of those ingredients are cetyl trimethly ammonium chloride, stear trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

Concentration of one or more surfactants in dyeing composition is in the range of 0.1 to 20%, preferably 0.2 to 15% and most preferably 0.2-10% by weight, calculated to the total composition.

Compositions of the present invention can comprise an organopolysiloxane wherein at least one silicium atom is linked to an alkylene group having a hetero-atom, in particular a nitrogen atom, with a poly-(N-acyl alkyleneimine) units of the formula

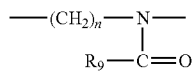

wherein n is a number from 1 to 5 and $R_9$ is hydrogen, a $C_1$-$C_{12}$-alkyl or cycloalkyl, aralkyl or aryl group. Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

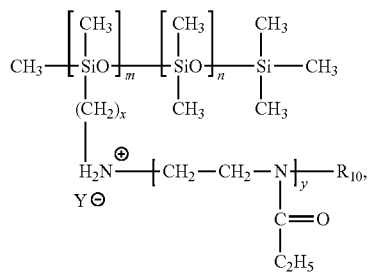

wherein m and n each are numbers from 20 to 10,000, in particular 50 to 7,000, especially 100 to 5,000, x is a number between 1 and 5, preferably 3, and y is a number from 5 to 30, $R_{10}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Another preferred compound in the composition of present invention especially in bleaching and/or highlighting composition and in dyeing composition is ceramide type of compounds according to general formula

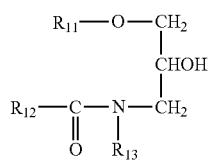

where $R_{11}$ and $R_{12}$ are independent from each other alkyl- or. alkenyl group with 10 to 22 carbon atoms, $R_{13}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide. Concentration of ceramide type of compounds ranges from 0.01 to 2%, preferably 0.01 to 1% yb weight calculated to total composition before mixing.

The compositions of the present invention can comprise of at least one ubiquinone of the formula (I)

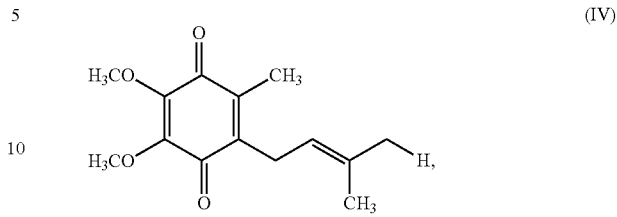

wherein n is a number from 1 to 10. Concentration of ubichinone can vary between 0.001% and 10% by weight, calculated to the total composition before mixing.

Compositions of the present invention may comprise synthetic mica coated with metal oxide or oxides having a volume particle size distribution in the range of 1 to 750 μm. Use of synthetic mica coated with metal oxide or oxides mainly in decorative cosmetics is disclosed in an international patent application of Sun Chemical Corporation published with a number WO 2005/065632 A1. In the document synthetic mica and coated synthetic mica with at least one metal oxide or oxides is disclosed in detail. The content of the document is included herewith by reference.

Suitable metal oxide or oxides for coating synthetic mica are titanium dioxide, chromium oxide, ferric oxide or mixtures thereof. In the present invention the preferred is synthetic mica coated with titanium dioxide. Such materials are commercially available from Sun Chemical Corporation and Merck (Timiron Synwhite 40) and known with their INCI names Synthetic Fluorphologopite The volume particle size distribution of synthetic mica coated with a metal oxide or oxides is in the range of 1 to 750 μm, preferably 1 to 250 μm, more preferably 1 to 100 μm and most preferably 5 to 95 μm. The particle sizes referred are relating to the volume particle size distribution meaning that particles found in the coated synthetic mica having volume particle size in the given ranges.

Concentration of synthetic mica coated with at least metal oxide or oxides is from 0.01 to 20%, preferably 0.1 to 15%, more preferably 0.25 to 10% and most preferably 0.5 to 55% by weight calculated to total composition.

Compositions may further comprise additional substances found in lightening and/or coloring compositions for hair such as fragrance, humectants, chelants and radical scavengers.

The following examples are to illustrate the invention but not to limit it.

Example 1

Bleaching—Colouring Powder Composition—Part A

| | |
|---|---|
| Hydroxyethylcellulose | 1.40 % by weight |
| Cellulose gum | 3.20 |
| Xanthan gum | 0.30 |
| Tetrasodium EDTA | 2.00 |
| Sodium carbonate | 1.00 |
| Ammonium persulfate | 21.00 |
| Potassium persulfate | 46.60 |
| Sodium metasilicate | 10.20 |
| Corn starch | 1.10 |

-continued

| | |
|---|---|
| Diatomaceous Earth | 11.10 |
| Polyquaternium-10 | 0.10 |
| Silica* | 1.00 |
| Synthetic fluorphologopite** | 1.00 |
| Basic Yellow 87 | 0.10 |

*Aerosil 380
**Synthetic fluorphologopite used is commercially available from Sun Chemical Corporation under the trade name SunShine Glitter White with a particle size distribution in the range of 20 to 95 μm.

The above composition is prepared by combining all powder components together and by mixing until homogeneity in a suitable mixer.

Oxidizing Lotion—Part B

| | |
|---|---|
| Hydrogen peroxide | 9.00 (% by wt.) |
| Cetyl stearyl alcohol | 1.70 |
| Phosphoric acid | 0.50 |
| Sodium lauryl sulfate | 0.20 |
| Coenzyme Q10 | 0.05 |
| Cetyl PG hydroxyethyl palmitamide | 0.10 |
| Disodium hydrogen phosphate | 0.10 |
| Salicylic acid | 0.10 |
| Water | ad 100.00 |

Oxidizable Solvent Composition—Part C

| | |
|---|---|
| Benzyl alcohol | 100 |

Form the above three compositions a ready to use composition was prepared as follows:

| | Inventive | Comparative |
|---|---|---|
| Part A | 5 g | 5 g |
| Part B | 7 g | 7 g |
| Part C | 0.36 g | — |
| Water | — | 0.36 g |

Both compositions were used to bleach and colour human hair at 40° C. for 30 min. After rinsing and drying hair, I, a and b values were measured and using the initial values the colour differences (ΔE) were calculated. The following results were obtained.

| | ΔE |
|---|---|
| Inventive | 33.8 |
| Comparative | 22.5 |

From the above it is clear that inventive composition colours hair much stronger than the comparative composition owing to its Benzyl alcohol content.

Example 2

In the powder bleach-colour composition of Example 1 the basic yellow 87 was replaced with the same concentration of Basic red 51. The bleaching-colouring was carried out in the same way as in Example 1. The following results were obtained.

| | ΔE |
|---|---|
| Inventive | 44.9 |
| Comparative | 19.6 |

The above results confirm again that the inventive composition colours hair much stronger than the comparative composition.

Similar results were observed when benzyl alcohol was replaced with each of isopropanol, 2-phenoxyethanol, or 2-benzyloxyethanol.

Example 3

In the powder bleach-colour composition of Example 1 the basic yellow 87 was replaced with the same concentration of the dye with the following chemical structure;

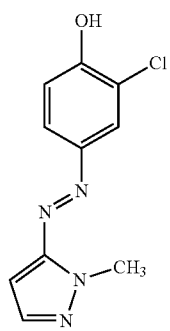 [SMILES: Cn1nccc1/N=N/c1ccc(O)c(Cl)c1]

The bleaching-colouring was carried out in the same way as in Example 1. The following results were obtained.

| | ΔE |
|---|---|
| Inventive | 51.9 |
| Comparative | 11.2 |

The above results confirm again that the inventive composition colours hair much stronger than the comparative composition.

Similar results were observed when benzyl alcohol was replaced with each of isopropanol, 2-phenoxyethanol, or 2-benzyloxyethanol.

The invention claimed is:

1. A method for bleaching and colouring hair comprising steps (1) and (2) in order:
   (1) preparing an aqueous composition by mixing immediately before use three separate Parts (A)-(C), wherein
      Part (A) is an anhydrous composition comprising at least one direct dye, at least one compound with hair bleaching effect and at least one alkalizing agent, and
      Part (B) is an aqueous composition comprising at least one oxidizing agent, and
      Part (C) is a composition comprising at least one oxidizable solvent, and
   (2) applying the aqueous composition obtained in step (1) onto hair, and
   (3) rinsing off the aqueous composition from the hair after processing for between 5 to 45 min.

2. A kit for bleaching and colouring hair comprising three separate compositions, wherein:

a first composition, Part (A), is an anhydrous composition and comprises at least one direct dye, at least one compound with hair bleaching effect and at least one alkalizing agent, and a second composition, Part (B), is an aqueous composition comprising at least one oxidizing agent, and a third composition, Part (C), comprises at least one oxidizable solvent.

3. The method of claim 1, wherein the at least one direct dye is selected from the group consisting of a nitro dye, Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87, Basic Orange 31, Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9, Disperse Violet 1, alkali metal salts of the foregoing direct dyes, a plant dye, and a compound having the structural formula (I), (II), (III) or (IV):

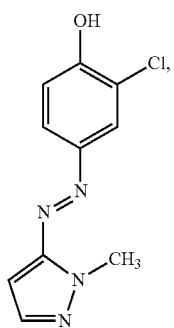

Formula (I)

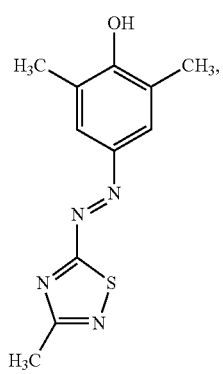

Formula (II)

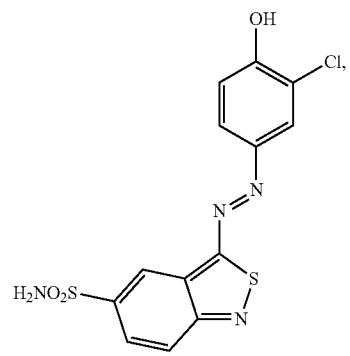

Formula (III)

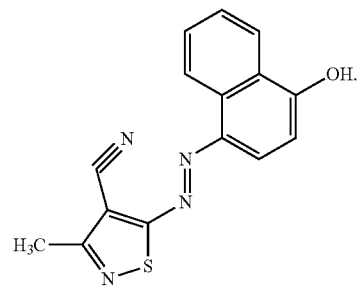

Formula (IV)

4. The method of claim 1, wherein the one compound with bleaching effect is selected from the group consisting of sodium persulphate, potassium persulphate and ammonium persulphate or their mixtures.

5. The method of claim 1, wherein the at least one direct dye is selected from cationic, anionic and nonionic dyes.

6. The method of claim 1, wherein the at least one oxidizing agent is hydrogen peroxide.

7. The method of claim 1, wherein the at least one alkalizing agent is sodium metasilicate.

8. The method of claim 1, wherein the at least one oxidizable solvent is an aromatic or aliphatic alcohol.

9. The method of claim 1, wherein the at least one oxidizable solvent is selected from the group consisting of 2-phenoxyethanol, benzyl alcohol, 2-phenylethanol, 2-benzyloxyethanol, isopropanol, propanol, n-butanol, isobutanol, t-butanol and 1-pentanol.

10. The method of claim 1, wherein the alkali metal salt is a sodium salt or a potassium salt.

11. The method of claim 1, wherein the at least one direct dye is selected from the group consisting of a nitro dye, Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87, Basic Orange 31, Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No.

33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9, Disperse Violet 1, alkali metal salts of the foregoing direct dyes, a plant dye, and a compound having the structural formulas (I), (II), (III) or (IV).

12. The kit of claim 2, wherein the at least one direct dye is selected from the group consisting of a nitro dye, Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87, Basic Orange 31, Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9, Disperse Violet 1, alkali metal salts of the foregoing direct dyes, a plant dye, and a compound having the structural formula (I), (II), (III) or (IV):

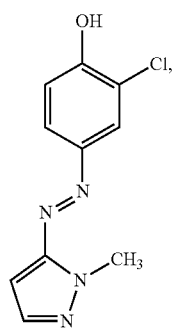

Formula (I)

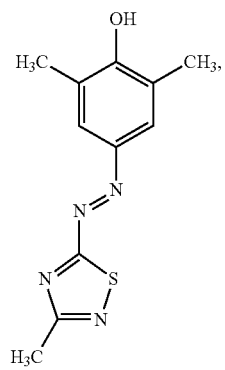

Formula (II)

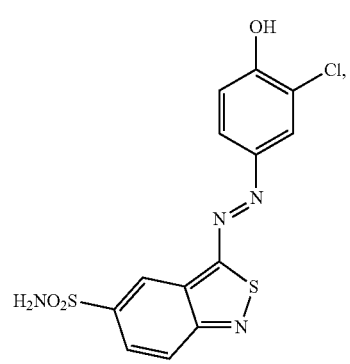

Formula (III)

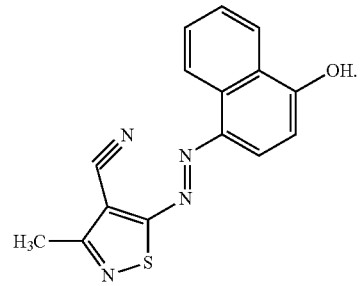

Formula (IV)

13. The kit of claim 2, wherein the one compound with bleaching effect is selected from the group consisting of sodium persulphate, potassium persulphate and ammonium persulphate or their mixtures.

14. The kit of claim 2, wherein the at least one direct dye is selected from cationic, anionic and nonionic dyes.

15. The kit of claim 2, wherein the at least one oxidizing agent is hydrogen peroxide.

16. The kit of claim 2, wherein the at least one alkalizing agent is sodium metasilicate.

17. The kit of claim 2, wherein the at least one oxidizable solvent is an aromatic or aliphatic alcohol.

18. The kit of claim 2, wherein the at least one oxidizable solvent is selected from the group consisting of 2-phenoxyethanol, benzyl alcohol, 2-phenylethanol, 2-benzyloxyethanol, isopropanol, propanol, n-butanol, isobutanol, t-butanol and 1-pentanol.

19. The kit of claim 2, wherein the alkali metal salt is a sodium salt or a potassium salt.

20. The kit of claim 2, wherein the at least one direct dye is selected from the group consisting of a nitro dye, Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87, Basic Orange 31, Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9, Disperse Violet 1, alkali metal salts of the foregoing direct dyes, a plant dye, and a compound having the structural formulas (I), (II), (III) or (IV).

* * * * *